United States Patent
Currier et al.

(10) Patent No.: US 12,324,436 B2
(45) Date of Patent: Jun. 10, 2025

(54) PROTECTIVE ANTIMICROBIAL SYSTEM

(71) Applicant: Performance Chemicals LLC, Franklin, NH (US)

(72) Inventors: Michael Currier, Gilford, NH (US); Matthew Currier, Gilford, NH (US); Sarah A. Currier, Sanbornton, NH (US); Robert Currier, Canterbury, NH (US)

(73) Assignee: Performance Chemicals LLC, Franklin, NH (US)

( * ) Notice: Subject to any disclaimer, the term of this patent is extended or adjusted under 35 U.S.C. 154(b) by 463 days.

(21) Appl. No.: 17/910,195

(22) PCT Filed: Mar. 5, 2021

(86) PCT No.: PCT/US2021/021114
§ 371 (c)(1),
(2) Date: Sep. 8, 2022

(87) PCT Pub. No.: WO2021/194728
PCT Pub. Date: Sep. 30, 2021

(65) Prior Publication Data
US 2023/0129445 A1 Apr. 27, 2023

Related U.S. Application Data (60) Provisional application No. 63/081,419, filed on Sep. 22, 2020, provisional application No. 63/000,924, filed on Mar. 27, 2020.

(51) Int. Cl.
| | | |
|---|---|---|
| *A01N 59/20* | (2006.01) | |
| *A01N 25/02* | (2006.01) | |
| *A01N 25/34* | (2006.01) | |
| *A01N 59/02* | (2006.01) | |
| *A01P 1/00* | (2006.01) | |

(52) U.S. Cl.
CPC ............ *A01N 59/20* (2013.01); *A01N 25/02* (2013.01); *A01N 25/34* (2013.01); *A01N 59/02* (2013.01); *A01P 1/00* (2021.08)

(58) Field of Classification Search
CPC ........ A01N 59/20; A01N 25/02; A01N 25/34; A01N 59/02; A01P 1/00; A61L 2202/13; A61L 2/18; A61L 2/232; A61L 2/238; Y02A 50/30; A61K 33/02; A61K 33/34; A61K 2300/00; A61P 31/00
See application file for complete search history.

(56) References Cited

U.S. PATENT DOCUMENTS

| | | |
|---|---|---|
| 5,213,803 A | 5/1993 | Pollock et al. |
| 5,645,846 A | 7/1997 | Oka et al. |
| 5,830,526 A | 11/1998 | Wilson et al. |
| 6,264,936 B1 | 7/2001 | Sawan et al. |
| 6,627,229 B2 | 9/2003 | Kikuchi et al. |
| 7,981,408 B2 | 7/2011 | Schroeder et al. |
| 7,989,043 B2 | 8/2011 | Salemi et al. |
| 8,127,922 B2 | 3/2012 | Nordholm et al. |
| 8,778,386 B2 | 7/2014 | Liu et al. |
| 9,265,259 B2 | 2/2016 | Tu et al. |
| 2003/0091767 A1 | 5/2003 | Podhajny |
| 2006/0008379 A1 | 1/2006 | Mielnik et al. |
| 2007/0190119 A1 | 8/2007 | Salemi et al. |
| 2009/0110751 A1 | 4/2009 | Kenneke |
| 2011/0027399 A1 | 2/2011 | Shimamoto et al. |
| 2014/0051732 A1 | 2/2014 | Ghannoum et al. |
| 2015/0031729 A1 | 1/2015 | Ghannoum et al. |
| 2015/0320035 A1 | 11/2015 | Gauthier et al. |
| 2016/0166624 A1 | 6/2016 | Schwartz |
| 2017/0183545 A1 | 6/2017 | Kelleher |
| 2019/0357536 A1 | 11/2019 | Brommer |

FOREIGN PATENT DOCUMENTS

| | | |
|---|---|---|
| CN | 111557496 | 8/2020 |
| DE | 202020001666 | 6/2020 |
| EP | 467869 | 1/1992 |
| EP | 1537796 | 6/2005 |
| JP | H0970234 | 3/1997 |
| WO | 2007064343 | 6/2007 |
| WO | 2007145783 | 12/2007 |
| WO | 2013151569 A1 | 10/2013 |
| WO | 2019014424 A1 | 1/2019 |

OTHER PUBLICATIONS

International Search report and Written Opinion in PCT/US21/21114 mailed May 11, 2021.
Borrow G et al: "Putting copper into action: Copper-impregnated products with potent biocidal activities", The ASEB Journal, vol. 18, No. 14, Jan. 1, 2004, pp. 1728-1730, XP009146575.
Philip Pells: "Copper as an Anti-Virus Skin Protector", May 21, 2020, pp. 1-10, XP093168629, Retrieved from the Internet: URL:https://www.pellsconsulting.com.au/downloads/COPPER%20AS%20ANTI%20VIRUS.pdf.
ESSR for EP 21 77 4787 dated Jun. 13, 2024.

*Primary Examiner* — Sue X Liu
*Assistant Examiner* — Nathan W Schlientz
(74) *Attorney, Agent, or Firm* — KPIP Law, PLLC; Kimberly A Peaslee (57) ABSTRACT

The system and method for providing antimicrobial and/or antiviral characteristics to substrates via an additive process for providing safe handling and reduction of cross contaminations from person to person from handling, shipping, storage and use of papers, boxes, liners, hospital barriers, respirator filters and liners, hospital curtains, masks, draperies, bed liners, and the like.

12 Claims, 6 Drawing Sheets

PROTECTIVE ANTIMICROBIAL SYSTEM

CROSS REFERENCE TO RELATED APPLICATIONS

This Application claims the benefit of U.S. Provisional Patent Application No. 63/000,924, filed Mar. 27, 2020, and U.S. Provisional Patent Application No. 63/081,419, filed Sep. 22, 2020, the contents of each of which are incorporated by reference herein in their entirety.

FIELD OF THE DISCLOSURE

The present disclosure relates to composite substrates and more particularly to substrates that exhibit antimicrobial and/or antiviral protective characteristics.

BACKGROUND OF THE DISCLOSURE

This process is designed to add protection from viral and bacterial growth, and to reduce or eliminate these microbial agents from being transferred from person to person, substrate to person, and substrate to substrate. Wherefore it is an object of the present disclosure to overcome the shortcomings and drawbacks associated with conventional substrates.

SUMMARY OF THE DISCLOSURE

One aspect of the present disclosure is an antimicrobial system, comprising: an outermost layer, comprising an antimicrobial compound; and a water-repellent layer being configured to eliminate and/or mitigate liquid phase of transfer to a person, a package, or a substrate being protected.

One embodiment of the antimicrobial system is wherein the antimicrobial compound comprises: a solution, the solution comprising: 47% ammonium sulfate; 42% water; and 11% other components; wherein the ammonium sulfate and water are mixed with a metallic sulfate and ammonium sulfamate blend and of the other components are surfactants totaling 1%, such that a resultant pH of a final solution is 5-6.

Another embodiment of the antimicrobial system is wherein the metallic sulfate is copper sulfate pentahydrate in a range of 4-6% and the ammonium sulfamate is about 1%.

Yet another embodiment of the antimicrobial system of claim 3, further comprising about 5% of triethanolamine (TEA) solution forming a dark blue solution. In certain embodiments, the antimicrobial system further comprises a defoamer and a soft soap. In some cases, 4 drops per pound of defoamer are added and 1% soft soap to create the final solution.

Still yet another embodiment of the antimicrobial system is wherein the antimicrobial solution is added to paint coating at about a 2.6% dry solids level which may be a uniform disbursement, and/or bloom to the surface of the coating when dried, cured, or catalyzed to achieve killing of bacteria and/or viruses. In some cases, the antimicrobial solution is topically applied to a non-woven substrate at a level of about 15% dry pick-up to achieve killing of bacteria and/or viruses. In certain embodiments, the antimicrobial solution is topically applied to a paper substrate at a level of about 15% dry pick-up to achieve immediate kill. In some cases, the antimicrobial system further comprises adding about 1-15% calcium carbonate into the paper substrate.

Still another embodiment of the antimicrobial system further comprises at least one additional layer between the outermost layer and the water-repellent layer. In some cases, the outermost layer further comprises a humectant.

Another aspect of the present disclosure is an antimicrobial system, comprising a solution, the solution comprising: 47% ammonium sulfate; 42% water; and 11% other components; wherein the ammonium sulfate and water are mixed with a metallic sulfate and ammonium sulfamate blend, and of the other components are surfactants totaling 1%, such that a resultant pH of the final solution is 5-6.

One embodiment of the antimicrobial system is wherein the metallic sulfate is copper sulfate pentahydrate in a range of 4-6% and the ammonium sulfamate is about 1%. In some cases, the antimicrobial system further comprises about 5% of triethanolamine (TEA) solution forming a dark blue solution. In certain cases, the antimicrobial system further comprises a defoamer and a soft soap.

Another embodiment of the antimicrobial system is wherein the antimicrobial solution is added to paint coating at about a 2.6% dry solids level which may be a uniform disbursement, and/or bloom to the surface of the coating when dried, cured, or catalyzed to achieve killing of bacteria and/or viruses.

Yet another embodiment of the antimicrobial system is wherein the antimicrobial solution is topically applied to a non-woven or paper substrate at a level of about 15% dry pick-up to achieve immediate kill.

Still yet another embodiment of the antimicrobial system further comprises adding about 1-15% calcium carbonate into the paper substrate.

Yet another aspect of the present disclosure is an antimicrobial system, comprising: an outermost layer, comprising an antimicrobial compound and a humectant; and a water-repellent layer being configured to eliminate and/or mitigate liquid phase of transfer to a person, a package, or a substrate being protected; wherein the antimicrobial compound comprises a solution, the solution comprising: 47% ammonium sulfate; 42% water; and 11% other components, the other components comprising a surfactant, a triethanolamine (TEA) solution, a defoamer, and a soft soap; wherein the ammonium sulfate and water are mixed with a metallic sulfate and ammonium sulfamate blend such that a resultant pH of a final solution is 5-6.

These aspects of the disclosure are not meant to be exclusive and other features, aspects, and advantages of the present disclosure will be readily apparent to those of ordinary skill in the art when read in conjunction with the following description, appended claims, and accompanying drawings.

BRIEF DESCRIPTION OF THE DRAWINGS

The foregoing and other objects, features, and advantages of the disclosure will be apparent from the following description of embodiments of the disclosure, as illustrated in the accompanying drawings in which like reference characters refer to the same parts throughout the different views. The drawings are not necessarily to scale, emphasis instead being placed upon illustrating the principles of the disclosure.

FIG. 5 shows the persistence of SARS-CoV-2 on six materials, where the results are provided in Median Tissue Culture Infectious Dose units ($TCID_{50}$)/mL.

DETAILED DESCRIPTION OF THE DISCLOSURE

One embodiment of the present disclosure is a system and method for providing antimicrobial and/or antiviral characteristics to substrates via an additive process for providing safe handling and reduction of cross contaminations from person to person from handling, shipping, storage, and use of such papers, boxes, liners, PPE: e.g., hospital barriers, hospital gowns, masks, respirator filters and liners, hospital curtains, draperies, bed liners; HVAC filers, ducts, duct liners, painted surfaces, and the like.

In one embodiment, a bacteria and/or virus resistant substrate (e.g., antimicrobial) comprises one or more of paper, textile, and non-wovens (e.g., hardwood, softwood, and recycled materials), including substrates selected from one or more of synthetic fibers, natural fibers, plus associated blends including spun bond, and fiberglass fibers. In certain embodiments, the substrate comprises a single layer. In some embodiments, the substrate comprises multiple layers which may be laminated or adhered to each other to increase rigidity and durability. In certain embodiments, a material comprising non-wovens may have directional and non-directional fiber alignments. In some cases, hardwood, soft wood, recycled papers, and such blends with synthetic fibers and synthetic fiber blends alone are useful for substrates.

One embodiment of the present disclosure provides antiviral (e.g., COVID-19) and/or antibacterial (e.g., strep, pneumonia) properties which have been applied onto substrates via an additive process for providing safe handling and a reduction of cross contaminations from person to person from handling, shipping, storage, and use of such papers, boxes, liners, PPE: e.g., hospital barriers, hospital gowns, masks, respirator filters and liners, hospital curtains, draperies, bed liners; HVAC filers, ducts, duct liners, painted surfaces, and the like.

In certain embodiments, the substrate materials (e.g., paper, textiles, and non-wovens) are compounded to include Calcium carbonate within the base fiber makeup or as core layers at concentrations of about 1-15%. In some cases, metals, metallics and blends thereof may be compounded into the substrate or as core layers. In one embodiment, the metal is copper. In one embodiment, the metal comprises silver, gold, copper sulfate, brass, or blended metals. In some cases, the metal is at a concentration of about 0.01-10% and is compounded into the substrate.

In one embodiment, a substrate is treated with a topical additive of: Ammonium Sulfate, Ammonium Sulfamate, Diammonium Phosphate, Monoammonium Phosphate, or the like. In some cases, the topical additive is applied at a level of 0.01-100% wt/wt. Depending on atmospheric moisture levels an additional humectant such as glycerin or a soap system may be added to increase moisture content to promote activity of protective antimicrobial systems of the present disclosure. In some cases, the humectant may be sodium xylene sulfonate, cocamide propyl betaine, amine oxides, nonylphenol ethoxylates, nonyl phenol green replacements, or the like.

Figure 1:
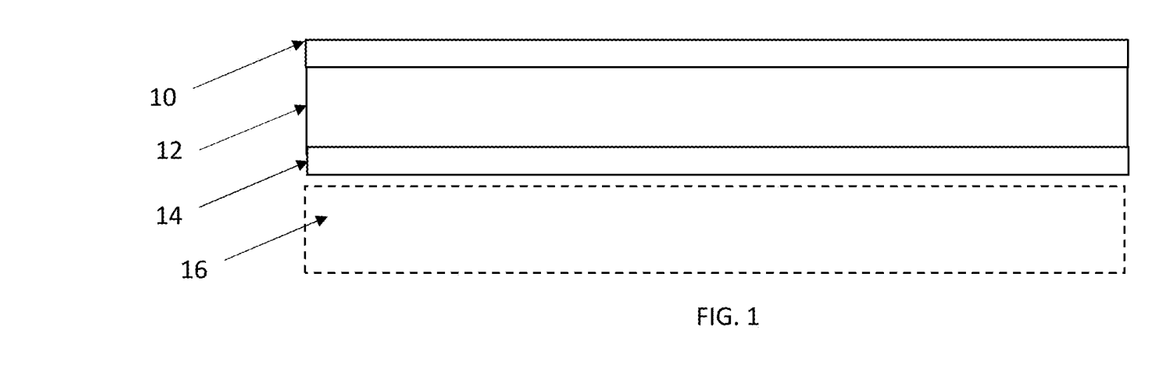
FIG. 1 shows a diagrammatic view of one embodiment of a protective antimicrobial system of the present disclosure.

Referring to FIG. 1, a diagrammatic view of one embodiment of a protective antimicrobial system of the present disclosure is shown. More specifically, a water-repellent layer 14 configured to eliminate and/or mitigate liquid phase of transfer to a person, a package, or a substrate being protected 16 is used. In some cases, an inner packaging core layer 12 comprises layers described in the parameters above. In some cases, the core layer comprises calcium carbonate, or the like, and metal or metallic additives within the same layer. One embodiment of a protective antimicrobial system has a top layer 10 comprising a material known as 838. It is understood that water transfer of the 838 and a virus (for example) and vice versa is needed to be effective. Where this coated material has hydrophilic properties, this eliminates virus propagation on the surface of traditional hydrophobic PPE materials used in the market today. In one study, the Canadian Microbiology Institute stated that COVID, and COVID-19 virus can survive 45 days when on plastic, glass, and hydrophobic surfaces.

Figure 2A:
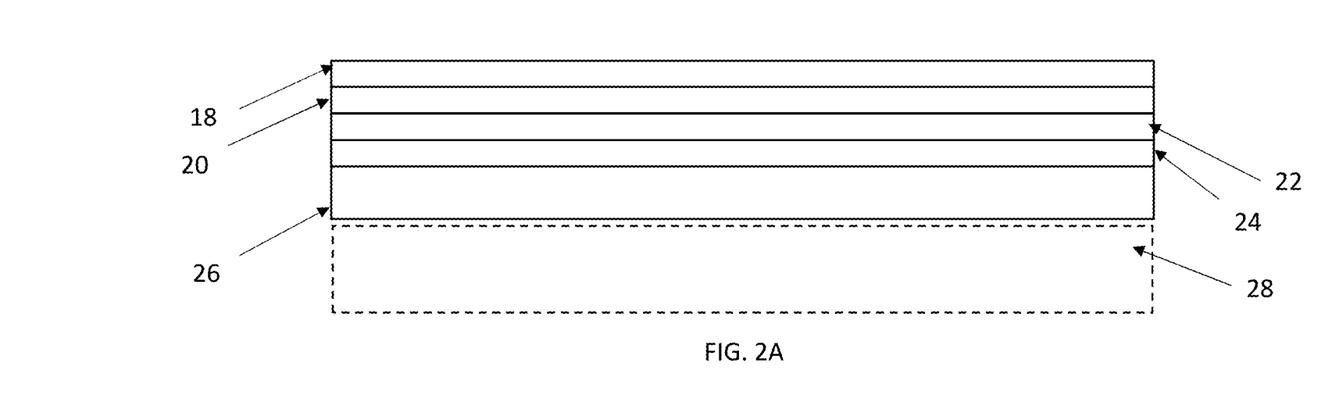
FIG. 2A shows a diagrammatic view of another embodiment of a protective antimicrobial system of the present disclosure.

Referring to FIG. 2A, a diagrammatic view of another embodiment of a protective antimicrobial system of the present disclosure is shown. More specifically, a water-repellent outer layer 26 configured to eliminate and/or mitigate the liquid phase of transfer is used. This layer, if present, is often adjacent a person, a package, or a substrate being protected 28. In some cases, there may be no water repellant layer. In some cases, one or more inner packaging core layer(s) 20, 22, 24 comprise layers described in the parameters above. In some cases, the core layers comprise a calcium carbonate layer 22, or the like, and a metal or metallic additive layer 24 within different layers. In some cases, these compounds are applied to a single layered sheet, non-woven mat, or to a single layered or multilayered textile with the same benefits. In certain embodiments, a topical layer may be included 18. In certain embodiments, a humectant layer is also present. In some cases, the humectant layer is combined with a topical layer 18 comprising 838, or the humectant is in a separate layer on top of the 838. It is to be understood that in some cases the various layers are distinct and in other cases, there are combination layers comprising one more of the various components to form the protective antimicrobial system.

For cases where the substrate is a non-woven, 838 is topically applied to a non-woven substrate at a level of about 15% dry pick-up to achieve killing of the microbes and/or viruses. For cases where the substrate is paper based, 838 is topically applied to a paper substrate at a level of about 15% dry pick-up to achieve immediate kill. In certain embodiments, the addition of about 1-15% calcium carbonate into the base sheet of paper is used.

With certain embodiments of the composition of the present disclosure applied to a substrate, the virus is mutated by using an ammonium sulfate solution (pH of 2-4), surfactant, and/or copper sulfate and/or zinc sulfate material to genetically disable the glycoproteins (crown component of the nano cell virus) through the same phase of water/hydration sharing. See, e.g., FIGS. 4A and 4B.

One embodiment of a composition of the present disclosure (i.e., 838) is produced by starting with a solution of about 40% ammonium sulfate (BO45). In one embodiment, the composition comprises about 47% BO45, about 42% water, and about 11% other components. In one embodiment, the BO45 and water are mixed with a metallic sulfate and ammonium sulfamate blend. In one embodiment the metallic sulfate is copper sulfate pentahydrate in a range of 4-6% and the ammonium sulfamate is about 1%. In one embodiment, about 5% of triethanolamine (TEA) solution, where 85% is mixed in and some may precipitate out, is added and a dark blue solution emerges. This solution is reacted to form a clear blue liquid. Next, surfactants totaling about 1% are added. In one embodiment, an antibacterial soft soap is added along with a defoamer, or $C_{11}$-$C_{15}$ linear alcohol, non-silicone, non-oil, or the like. In one case, 4 drops per pound of defoamer were added. In some cases, the resultant pH of the solution is about 5-6.

Figure 2B:
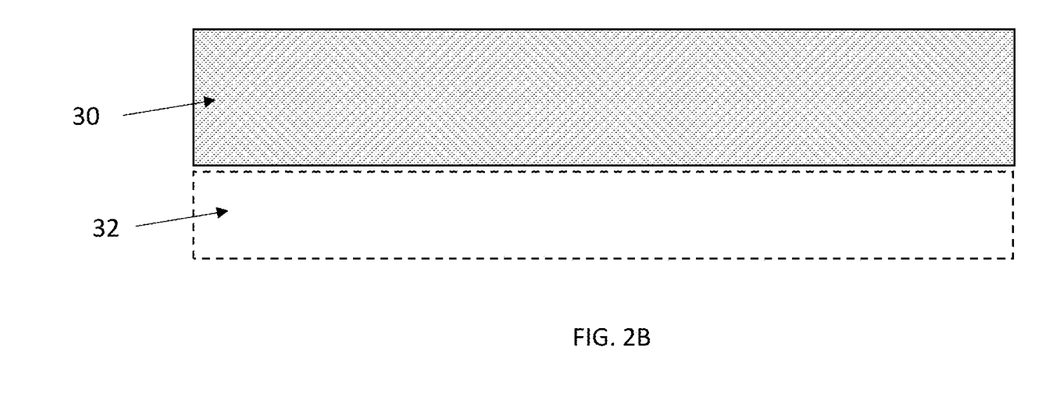
FIG. 2B shows a diagrammatic view of yet another embodiment of a protective antimicrobial system of the present disclosure.

Referring to FIG. 2B, a diagrammatic view of yet another embodiment of a protective antimicrobial system of the present disclosure is shown. More specifically, this embodiment (838) is applied to a substrate 32 as an additive to paint 30. This application may be a uniform disbursement, and/or bloom to the surface of the coating when dried, cured, or catalyzed. For cases where the substrate is paint, 838 is added into the paint at about 2.6% dry solids level to achieve performance. In one example, the base paint had a composition including calcium carbonate as a filler (e.g., Behr Marquis Exterior Paint).

In certain embodiments, a water repellent consisting of a C-6 based polytetrafluoroethylene (PTFE) dispersion combined with an acrylic copolymer (classified as "repellent") was added to a solution of 838 and water. In one embodiment, the repellent was added at about 3-4% and the 838 was diluted in water by about 50% to make R900. One embodiment of the repellent comprised water (about 16%), promex20s (1,2-benzisothiazolin-3-one) (about 0.2%), 20% active fatty acid defoamer (about 0.04%), C-6 PTFE repellent 30% active total solids (about 50%), and acrylic emulsion 50% active total solids (about 34%) to form a mixture having a pH of about 7-9.

In the case of the two non-woven materials treated with a highly water and grease resistant material, the R900, the 5xx0 and Non-Woven Ultra Sonic Bonded Spunlace, chemical treatment enhanced viral persistence on these surfaces compared to the untreated controls. With both materials, a significant change in surface properties was observed compared to the controls, where the applied inoculum remained in a spherical droplet on the deposited surface rather than being absorbed into the material. As a result, the drying time of the inoculum was significantly prolonged on the treated surfaces, likely contributing to the enhanced persistence of viable virus.

Embodiments of the protective antimicrobial substrate of the present disclosure were tested, where the survival of SARS-CoV-2 virus particles were assessed over a 24-hour time course on a panel of 12 surfaces, consisting of chemically treated and untreated samples of six different material types as shown in Table 1.

TABLE 1

Figure 3A:
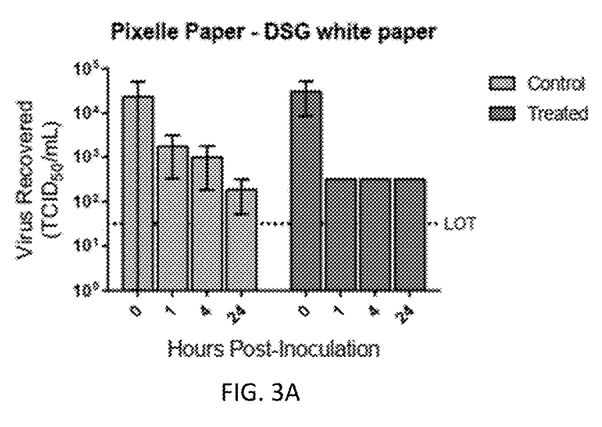
FIG. 3A-FIG. 3F are plots showing recovery of SARS-CoV-2 following inoculation of treated and untreated materials according to the principles of the present disclosure.
Figure 3B:
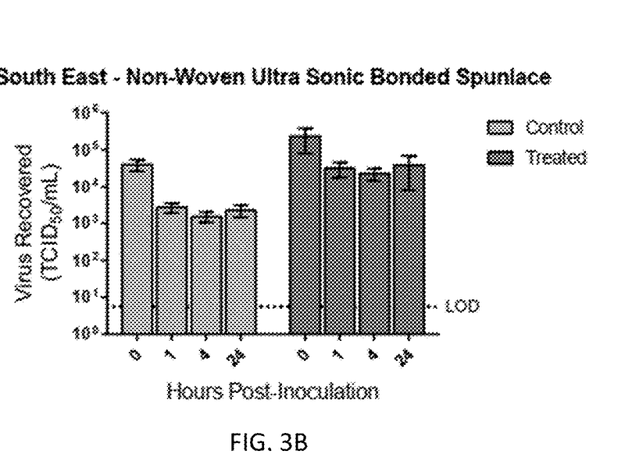
Figure 3C:
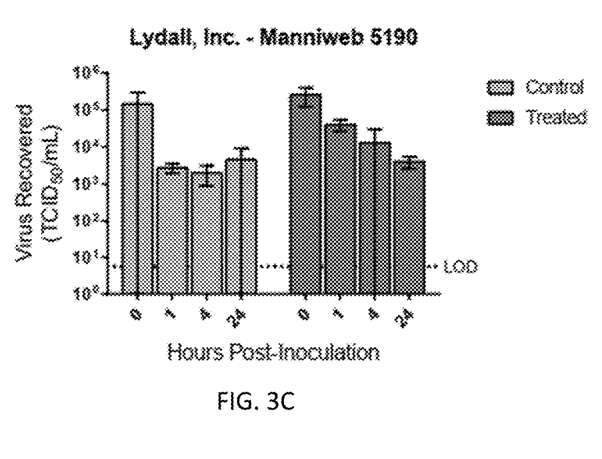
Figure 3D:
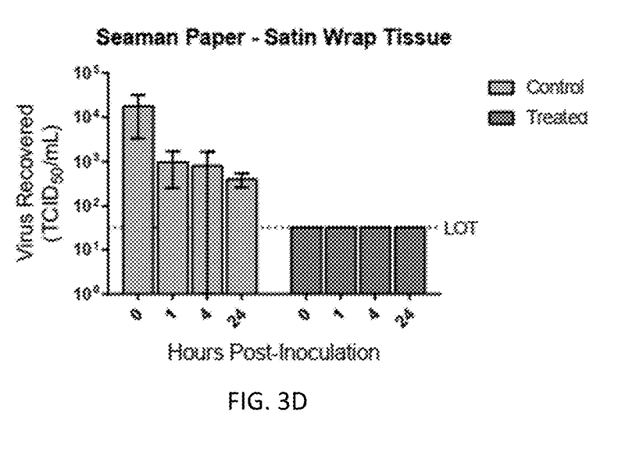
Figure 3E:
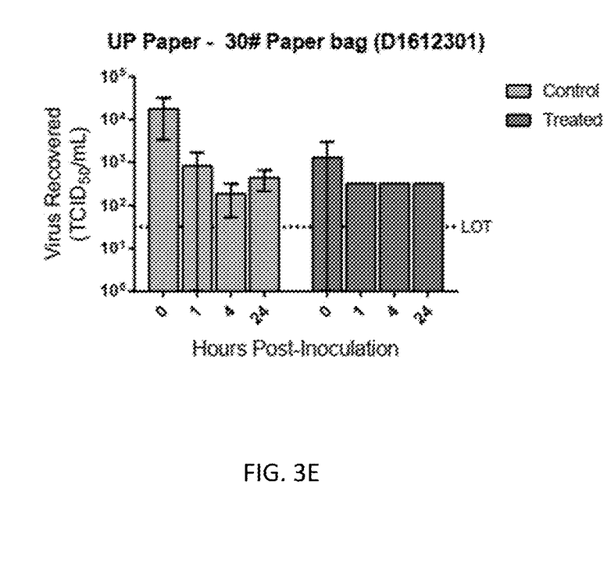

| Material | Type |
|---|---|
| Non-Woven sample (Lydall, Inc.-Manniweb 5190) - treated with R900 at about 15% wt/wt (FIG. 3C) | Non-woven materials |
| Non-Woven (Ultra Sonic Bonded Spunlace) - treated with R900 at about 15% wt/wt (FIG. 3B) | |
| UP Paper - 30# Paper bag (D1612301) - treated with 838 at 7.5% wt/wt (FIG. 3E) | |
| Seaman Paper - Satin Wrap #9 Tissue - treated with 838 at 15% wt/wt (FIG. 3D) | Paper-based materials |
| Pixelle Paper - DSG white paper - treated with 838 at 10% wt/wt (FIG. 3A) | |

TABLE 1-continued

Figure 3F:
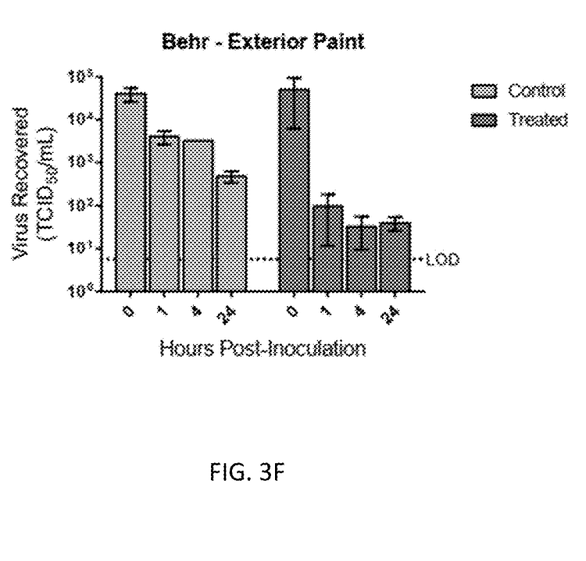

| Material | Type |
|---|---|
| BEHR exterior paint - treated with 838 at 3% wt/wt (FIG. 3F) | Paint |

In one embodiment, small (e.g., ~1 cm$^2$) coupons of the above-referenced materials were prepared under sterile conditions in a biosafety cabinet. Experimental inoculum was prepared using SARS-CoV-2 virus stocks with the addition of a tripartite soil load containing mucin, bovine serum albumin and tryptone as per ASTM standard, resulting in a suspension with a final virus concentration of about 4.5×106 $TCID_{50}$/mL.

The coupons were placed face-up on the surface of sterile petri dishes and spotted with a single ten-microliter droplet of the SARS-CoV-2 inoculum. Samples designated for immediate elution ("$T_0$") were transferred to individual wells of a sterile 12-well plate and eluted with 1 mL of virus culture medium (e.g., DMEM supplemented with 2% Fetal Bovine serum and 1% penicillin-streptomycin solution). Serial dilutions of eluates were subsequently prepared in virus culture medium and used to inoculate Vero E6 cells for end-point titration. The remaining samples were left to dry for one hour under the biosafety cabinet, and subsequently transferred to individual wells of 12-well culture plates. Samples designated for elution at the 1-hour time point ($T_1$) were processed as described above, while plates containing the $T_4$ and $T_{24}$ samples were removed from the biosafety cabinet and placed in a covered container, in the dark and at ambient temperature, for the appropriate amount of time until elution.

As a toxicity control, non-inoculated coupons of all material types were similarly eluted in 1 mL of culture medium to assess for residual toxicity from the materials themselves; determining the limits of detection (termed limit of toxicity) for each material type in cell culture. None of the eluates from untreated materials led to toxicity in cell culture.

With the paper-based materials, eluates of the chemically treated samples caused a cytotoxic effect in cell culture at both neat and 10:1 dilution, leading to a higher limit of detection for those materials as virus-induced cytopathic effect would not be discernable in the background of such cytotoxicity.

The effect of chemical treatment on SARS-CoV-2 persistence on various materials varied among the different material types, enhancing persistence in some cases while decreasing it in others. The detrimental effects of chemical treatment on SARS-CoV-2 surface stability were most pronounced with Seaman Paper-Satin Wrap Tissue (FIG. 3D), where the virus appeared immediately inactivated following inoculation on the chemically treated satin wrap (T=0) compared to the untreated control material. A similar result was observed with the treated Behr Paint sample (FIG. 3F), which showed a notable decrease in residual viable virus compared to the untreated control starting at 1-hour post-inoculation. This trend remained for the duration of the experiment up to the final 24-hour sampling point. This demonstrates the importance of having moisture transfer between 838 and virus/microbe (and vice versa) to kill on contact.

In the case of the two non-woven materials, one by Lydall, Inc. (Manniweb 5190) and a South East Non-Woven Ultra Sonic Bonded Spunlace, chemical treatment enhanced viral persistence on these surfaces compared to the untreated controls. With both materials, a significant change in surface properties was observed compared to the controls. There, the applied inoculum (R900) remained in a spherical droplet on the deposited surface rather than being absorbed into the material. As a result, the drying time of the inoculum was significantly prolonged on the treated surfaces, likely contributing to the enhanced persistence of viable virus.

Of note, another potential source of variation in the data may be attributed to loss of input inoculum onto the petri dish prior to transferring the coupons to 12-well plates. This was especially noted in the case of paper-based products, where the inoculum quickly soaked through the material and contacted the plastic plate below. The decision to carry out the assay in this way, rather than inoculate the coupons directly in a 12-well plate format, was to ensure that any recovered virus was directly attributed to the eluted material itself rather than being artificially deposited onto the plastic well surface in the process. However, as all materials were treated in the identical manner, this potential for variation and input sample loss was consistent for both control and treated materials.

Referring to FIG. 3A-FIG. 3F, recovery of SARS-CoV-2 following inoculation of treated and untreated materials according to the principles of the present disclosure is shown. More specifically, coupons of test materials were inoculated with 10 µl of SARS-CoV-2 suspended in a tripartite soil load and assessed for viral recovery immediately following inoculation (T=0 hrs) and after 1, 4, and 24 hours, respectively. Virus recovery was determined through the 50% tissue culture infectious dose assay (i.e., $TCID_{50}$) in Vero E6 cells following elution of inoculated materials in cell culture medium and subsequent 10-fold serial dilutions. Non-inoculated coupons of treated and control materials were utilized to determine assay limits of detection based on toxicity. In these cases, limits of toxicity ("LOT") are indicated in FIG. 3A-FIG. 3F, as compared with the assay limit of detection ("LOD") of the $TCID_{50}$ assay indicated for other materials without associated cytotoxicity. Results indicate means+/−standard deviations of three technical replicates of each material from a single experiment.

Figures 4A, 4B:
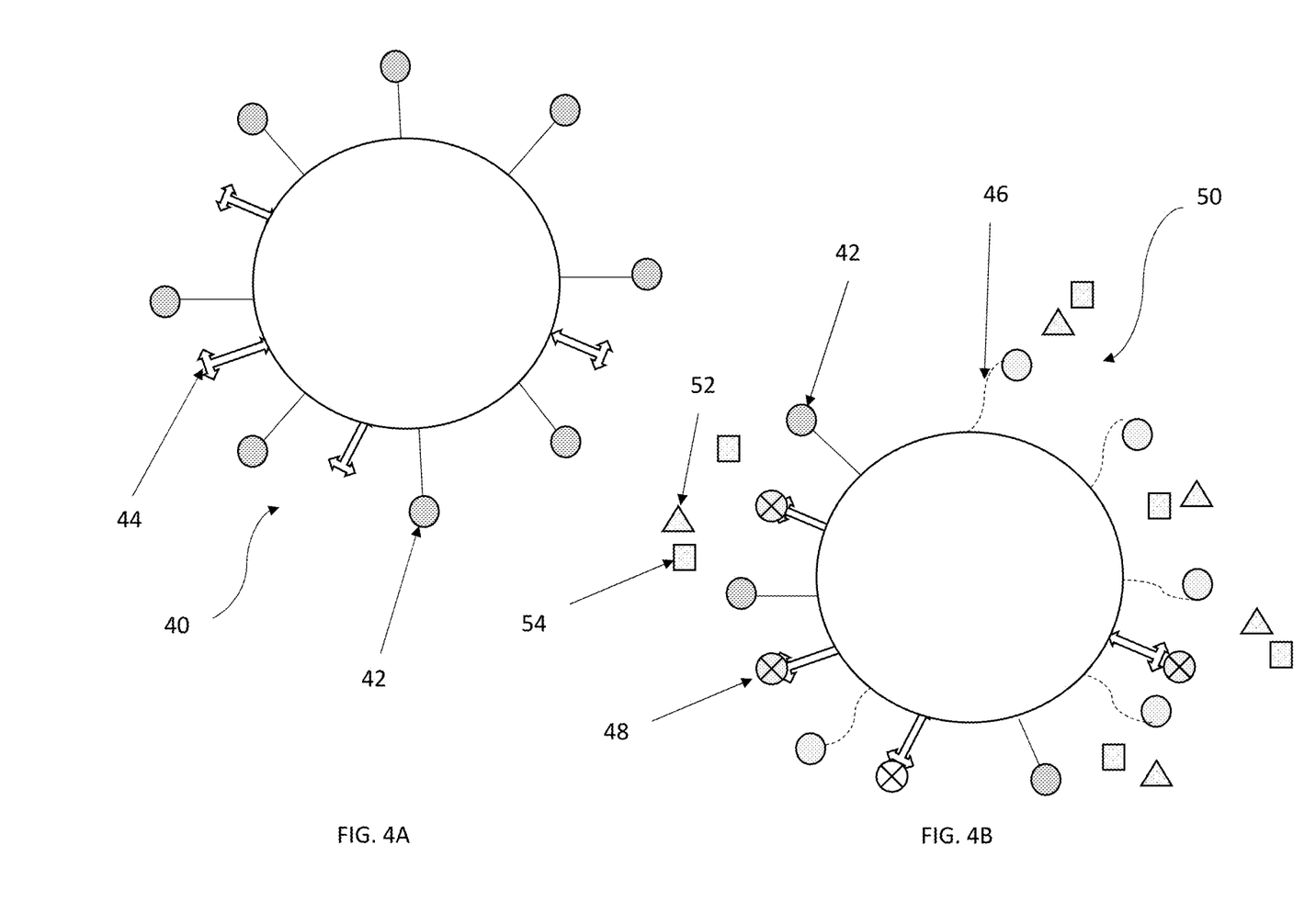
FIG. 4A is a diagrammatic view of an infectious SARS-CoV-2 virus particle.
FIG. 4B is a diagrammatic view of a weakened SARS-CoV-2 virus particle according to the principles of the present disclosure.

Referring to FIG. 4A, a diagrammatic view of an untreated infectious SARS-CoV-2 virus particle is shown. More specifically, the virus particle 40 has a plurality of glycoprotein spikes 42 and a plurality of hemagglutinin esterase dimers (HE) 44 distributed on the surface of the viral particle.

Referring to FIG. 4B, a diagrammatic view of a treated (weakened) SARS-CoV-2 virus particle according to the principles of the present disclosure is shown. More specifically, the virus particle 50 has some normal glycoprotein spikes 42, but also has some damaged glycoprotein spikes 46 and a weakened capsid after addition through moisture transfer of compositions according to the principles of the present disclosure. One such composition is 838 54. Through introduction of the 838, or the like, and the potential addition of a hydrophilic surfactant or blend (e.g. $C_{64}H_{124}O_{26}$) plus a silicon polyether super wetter surfactant (e.g., $(C_2H_4O)_nC_{11}H_{30}O_3Si_3$) enables the water/sugar, sugar/water transfer of the virus and 838, and vice versa. Both the (HE) structure and the Glycoprotein/Capsids damage weakening the virus enough to kill it upon contact by altering the amino acid group of the RNA core. As the OH and H interact from the moisture transfer it kills and sterilizes the virus and inhibits the virus propagation via deprotonation/protonation interactions. Also, with surfactants present in the 838 formulation this will break down the carbon shell of the protein thus aiding the kill rate of the virus 52, or the like. Through the moisture transfer between the chemistry and the virus cell, this will enable the ammonium sulfate, surfactant, and the copper sulfate to react within the glycoproteins outer strand and with the reaction to the ammonium sulfate transfer and metallic copper sulfate absorption interaction rendering the cell unable to bond and attack the host cell due to the essential dewatering and chemical interaction forming iron oxide and copper oxides through the pH reaction from the acid to the alkaline range with the generation of ammonia from the reaction of the sulfuric backbone of the ammonium sulfate and the calcium carbonate.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

The foregoing description of the embodiments of the present disclosure has been presented for the purposes of illustration and description. It is not intended to be exhaustive or to limit the present disclosure to the precise form disclosed. Many modifications and variations are possible in light of this disclosure. It is intended that the scope of the present disclosure be limited not by this detailed description, but rather by the claims appended hereto.

A number of implementations have been described. Nevertheless, it will be understood that various modifications may be made without departing from the scope of the disclosure. Although operations are depicted in the drawings in a particular order, this should not be understood as requiring that such operations be performed in the particular order shown or in sequential order, or that all illustrated operations be performed, to achieve desirable results.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. Modifications and substitutions by one of ordinary skill in the art are considered to be within the scope of the present disclosure.

What is claimed:

1. An antimicrobial system, comprising:
    a substrate having a plurality of layers, said plurality of layers comprising:
    an antimicrobial composition, calcium carbonate, and a water-repellent layer, said antimicrobial composition as a solution has a pH of 5-6 and comprises about 47% wt/wt ammonium sulfate, about 42% wt/wt water, and about 11% wt/wt other components, said other components comprising a metallic sulfate and ammonium sulfamate blend and 1% wt/wt surfactants with respect to the total weight of the antimicrobial composition; and wherein the water-repellent layer configured to eliminate and/or mitigate liquid phase from transferring from the substrate to an object being protected.

2. The antimicrobial system of claim 1, wherein the metallic sulfate is copper sulfate pentahydrate in a range of 4-6% wt/wt and the ammonium sulfamate is about 1% wt/wt of the about 11% wt/wt of the other components.

3. The antimicrobial system of claim 2, wherein an about 5% wt/wt of triethanolamine (TEA) solution is added to the antimicrobial composition as part of the about 11% wt/wt of the other components and about 85% of the about 5% wt/wt TEA solution mixes in, while a remainder precipitates out, forming a dark blue solution.

4. The antimicrobial system of claim 3, wherein the antimicrobial composition further comprises a defoamer and a soft soap as part of the about 11% wt/wt of the other components.

5. The antimicrobial system of claim 4, wherein the defoamer is about 4 drops per pound (2.2 kg) and the soft soap is about 1% wt/wt.

6. The antimicrobial system according to claim 1, wherein the antimicrobial composition is applied as a coating for a paint substrate at a level of about 2.6% wt/wt dry solids, the coating may comprise a uniform disbursement, and/or bloom to the surface when dried, cured, or catalyzed to achieve killing of bacteria and/or viruses.

7. The antimicrobial system according to claim 1, wherein the antimicrobial composition is topically applied as a coating to a nonwoven substrate at a level of about 7.5% wt/wt dry pick-up to achieve killing of bacteria and/or viruses.

8. The antimicrobial system according to claim 1, wherein the antimicrobial composition is topically applied as a coating is to a paper substrate at a level of about 15% wt/wt dry pick-up to achieve killing of bacteria and/or viruses.

9. The antimicrobial system according to claim 8, wherein the paper substrate comprises the calcium carbonate at about 1-15% wt/wt.

10. The antimicrobial system according to claim 1, wherein said plurality of layers comprises an outermost layer and at least one additional layer between the outermost layer and the water-repellent layer.

11. The antimicrobial system according to claim 1, wherein said plurality of layers comprises an outermost layer and the outermost layer further comprises a humectant.

12. The antimicrobial system according to claim 11, wherein the other components further comprise a triethanolamine (TEA) solution, a defoamer, and a soft soap.

* * * * *